(12) United States Patent
Kocher et al.

(10) Patent No.: US 11,051,709 B2
(45) Date of Patent: Jul. 6, 2021

(54) KNOWLEDGE DISCOVERY BASED ON BRAINWAVE RESPONSE TO EXTERNAL STIMULATION

(71) Applicant: IDEAL INNOVATIONS INCORPORATED, Arlington, VA (US)

(72) Inventors: Robert Kocher, McLean, VA (US); Loran Ambs, Williamsburg, VA (US)

(73) Assignee: IDEAL INNOVATIONS INCORPORATED, Arlington, VA (US)

( * ) Notice: Subject to any disclaimer, the term of this patent is extended or adjusted under 35 U.S.C. 154(b) by 134 days.

(21) Appl. No.: 16/363,402

(22) Filed: Mar. 25, 2019

(65) Prior Publication Data
US 2019/0216356 A1 Jul. 18, 2019

Related U.S. Application Data

(63) Continuation of application No. 14/571,583, filed on Dec. 16, 2014, now Pat. No. 10,238,310.

(60) Provisional application No. 61/916,331, filed on Dec. 16, 2013.

(51) Int. Cl.
| | |
|---|---|
| *A61B 5/0484* | (2006.01) |
| *A61B 5/04* | (2006.01) |
| *A61B 5/048* | (2006.01) |
| *A61B 5/00* | (2006.01) |

(52) U.S. Cl.
CPC .......... *A61B 5/04842* (2013.01); *A61B 5/048* (2013.01); *A61B 5/04012* (2013.01); *A61B 5/04845* (2013.01); *A61B 5/7246* (2013.01); *A61B 5/04847* (2013.01)

(58) Field of Classification Search
None
See application file for complete search history.

(56) References Cited

U.S. PATENT DOCUMENTS

| | | |
|---|---|---|
| 5,406,956 A | 4/1995 | Farwell |
| 6,238,338 B1 | 5/2001 | DeLuca |
| 7,565,193 B2 | 7/2009 | Laken |
| 8,014,847 B2 | 9/2011 | Shastri |
| 8,285,052 B1 | 10/2012 | Bhattacharyya |
| 2002/0062089 A1 | 5/2002 | Johnson |
| 2004/0048232 A1 | 3/2004 | Murphy |
| 2004/0143170 A1 | 7/2004 | DuRousseau |
| 2005/0089206 A1 | 4/2005 | Rice |
| 2005/0143629 A1 | 6/2005 | Farwell |
| 2005/0283053 A1 | 12/2005 | Decharms |
| 2006/0149139 A1 | 7/2006 | Bonmassar |
| 2006/0183981 A1 | 8/2006 | Skinner |
| 2007/0038035 A1 | 2/2007 | Ehrlich |
| 2007/0049844 A1 | 3/2007 | Rosenfeld |
| 2007/0100216 A1 | 5/2007 | Radcliffe |

(Continued)

*Primary Examiner* — Kaylee R Wilson
*Assistant Examiner* — Jay B Shah
(74) *Attorney, Agent, or Firm* — Butzel Long; Donald J. Lecher

(57) ABSTRACT

Techniques are disclosed for detecting knowledge based on brainwave response to external stimulation. A subject can be exposed to stimuli and brainwave responses indicating a p-300 signal can be detected. Further stimuli or sequences of stimuli can be selected be presented to the subject based on the category correlated with the stimuli that indicate a p-300 response.

22 Claims, 7 Drawing Sheets

(56) References Cited

U.S. PATENT DOCUMENTS

| | | |
|---|---|---|
| 2007/0191691 A1 | 8/2007 | Polanco |
| 2007/0249914 A1 | 10/2007 | Cacioppo |
| 2007/0255122 A1 | 11/2007 | Vol |
| 2008/0044799 A1 | 2/2008 | Krishna |
| 2008/0182231 A1 | 7/2008 | Cohen |
| 2008/0214902 A1 | 9/2008 | Lee |
| 2009/0024021 A1 | 1/2009 | George |
| 2009/0216091 A1 | 8/2009 | Arndt |
| 2012/0008955 A1 | 1/2012 | Shen |
| 2012/0089552 A1* | 4/2012 | Chang ............... G06N 5/02 706/52 |
| 2012/0197153 A1 | 8/2012 | Kraus |
| 2012/0245474 A1 | 9/2012 | Ofek |
| 2014/0163408 A1 | 6/2014 | Kocher |
| 2014/0163409 A1 | 6/2014 | Arndt |

\* cited by examiner

KNOWLEDGE DISCOVERY BASED ON BRAINWAVE RESPONSE TO EXTERNAL STIMULATION

This application claims priority to U.S. Provisional Application No. 61/916,331, filed Dec. 16, 2013, the disclosure of which is incorporated by reference in its entirety.

FIELD OF THE INVENTION

The present invention relates to psychophysiological measurement and, more specifically, to techniques for detecting knowledge based on brainwave response to external stimulation.

BACKGROUND

For decades Electroencephalography (EEG) and related tools that measure psychophysiological responses (e.g., polygraphs) have been used to discern whether someone is familiar with certain information. Examples of EEG tools include the systems and methods disclosed in U.S. Pat. No. 8,684,926 B2 and U.S. Patent Application publication 20140163409 A1 (each of which is incorporated by reference in its entirety). Systems such as these, are generally used in conjunction with the Guilty Knowledge Test (GKT). The purpose of the GKT is to associate the test subject to a particular event (e.g., a crime) by observation and interpretation of the test subject's psychophysiologic response when confronted with information that could only be known by someone familiar with the event.

Success of the GKT requires that the investigator know about the people, places or things associated with an event in order to pose verbal or non-verbal questions to the test subject. The investigator compares the test subject's psychophysiologic response to questions known to be related to the event with questions known to be unrelated to the event. The reliability of test results depends upon the test administrator's knowledge of what the test subject knows or is believed to know and subjective interpretation of observed psychophysiologic response of the test subject. There is a need for a non-verbal means of deducing what a person is familiar with by objective interpretation of psychophysiologic responses to that do not rely upon a priori knowledge of what the test subject knows.

SUMMARY OF THE INVENTION

In a first example, a method is disclosed for exposing a subject to a first sequence of stimuli. A subject is exposed to a first sequence of stimuli. At least one stimulus of the first sequence of stimuli correlated with a category. A brainwave response of the subject to the at least one stimulus of the first sequence of stimuli is detected. The detected brainwave response is correlated to at least one target category, and a second sequence of stimuli is selected, based upon the brainwave response of the subject to the at least one stimulus of the first sequence of stimuli.

In a second example, a system is disclosed that includes one or more sensors, a presentation device, and a processor. The processor is in communication with the presentation device and the at least one sensor and adapted and configured to send at least one stimulus in a first sequence of stimuli to the presentation device, receive a brainwave response from the at least one sensor based upon the brainwave response of a subject, correlate the detected brainwave response to at least one target category, and select a second sequence of stimuli, based upon the brainwave response of the subject to the at least one stimulus of the first sequence of stimuli.

For the purposes of this disclosure, a sequence of stimuli can be made up of a single stimulus or a set of stimuli.

DETAILED DESCRIPTION

Figure 1:
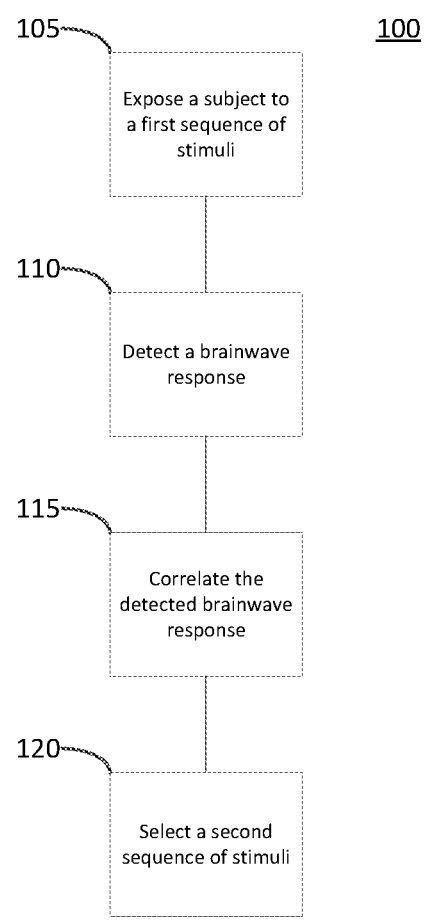
FIG. 1 shows a flow diagram for a first method for knowledge detection.

In contrast to the GKT described above, alternative techniques, such as those disclosed herein, do not require a priori knowledge of what the test subject knows. The knowledge of the test subject may be deduced without verbal questions by observing the psychophysiologic response of the subject to one or more sequences of stimuli (i.e. "decks") of information which may be selected based on the subject's responses to stimuli presented previously.

Research has established that a test subject's degree of familiarity with external stimuli such as images and sounds is correlated to strength and timing of brainwave signals observed by electroencephalograms (EEGs). The human brain can absorb and process stimuli at very high rates of presentation. Visual stimuli can be presented rapidly in a technique known as Rapid Serial Visual Presentation. In addition to images, alternative stimuli such as hearing stimuli, touch stimuli, smell stimuli, and taste stimuli may be presented using an analogous rapid serial presentation technique (collectively, the rapid serial presentation of any stimuli are referred to herein as "RSP"). The RSP technique typically displays stimuli to a test subject at rates of 4 to 12 stimuli per second. Depending upon the content and complexity of the information presented and the ability of the test subject to process the information, the presentation rate may be more or less than the typical values.

The brain processes stimuli and produces psychophysiologic response to recognition of the stimuli in the form of brainwaves observed by EEG. A response pattern strongly associated with recognition is the "p-300" brainwave which has a characteristic shape observed at about 300 milliseconds (ms) after being exposed to a recognized stimulus. EEG data time-tagged with the display of stimuli presented by the RSP technique enables a subject to be exposed to a large number of stimuli on a particular topic in a relatively short period of time. For instance, assuming a presentation pattern of 3 seconds of display followed by 3 seconds of rest, and a display rate of 8 images per second, a subject could be exposed to 240 images per minute.

EEG can be quantified in various ways by applying a Fourier transformation, including by amplitude, power, frequency, and in order to generate numerical values, ratios, or percentages; graphically display arrays or trends; and set thresholds. Many quantitative EEG measures can be used to quantify slowing or attenuation of faster frequencies in the EEG. These include the calculation of power within different frequency bands (i.e., delta, theta, alpha, and beta); ratios or percentages of power in specific frequency bands; and spectral edge frequencies (based on the frequency under which x % of the EEG resides). These discrete values can then be compared between different regions, such as hemispheres, or between electrode-pair channels. Time-compressed spectral arrays ("Spectrograms") incorporate both power and frequency spectrum data, and can be represented using color to show power at different frequencies. Additional measures include amplitude integrated EEG, which continuously monitors comatose patients by average ranges of peak-to-peak amplitudes displayed using a logarithmic scale, and the commercial Bispectral Index. Other nonparametric methods exist beyond Fourier transformation, including interval or period analysis and alternative transformation techniques. Parametric, mimetic, and spatiotemporal analyses are also available using a variety of computational methods and waveform analysis based on machine learning approaches trained on EEG recordings. Basic measures of total power can be quantified and compared to performance characteristics to identify correlations that can be used to predict the reoccurrence of those performance characteristics.

Figure 5:
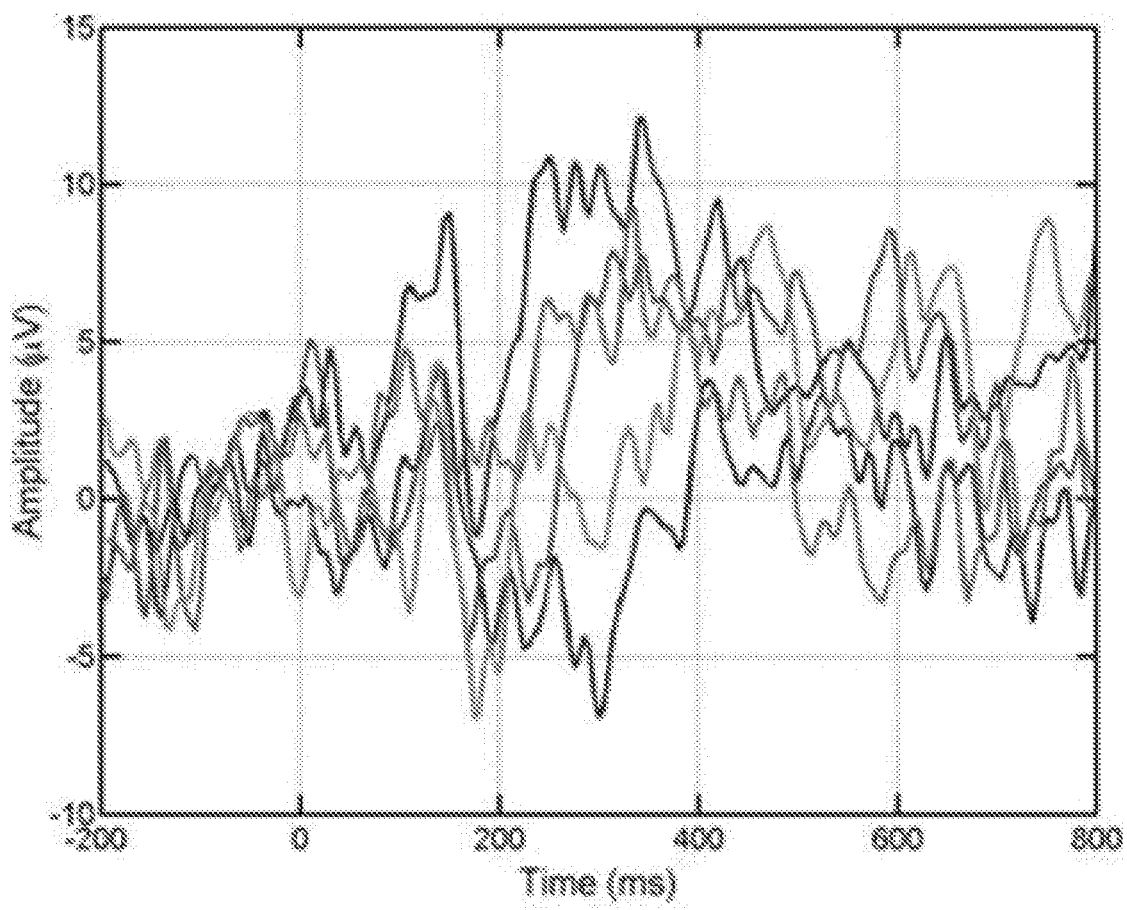
FIG. 5 shows multiple EEG time series illustrating the character and latency of p-300 signals.

Signal processing can discriminate between brainwave signals indicating recognition or familiarity with of the stimulus presented (e.g., images or sounds) and non-recognition or unfamiliarity with the stimuli. The character and latency of the p-300 varies by individual, the sense stimulated (e.g., visual, auditory), and with time for any particular individual. FIG. 5 illustrates an EEG time series of five visual target trials from a representative subject, and depicts the trial-to-trial variability of amplitudes and latencies for the p-300 component, Wang and Ding, Clinical Neurophysiology, Volume 122, Issue 5, May 2011, Pages 916-924.

Brainwave response to recognition also has repeatable and predictable characteristics which can be exploited by digital signal processing algorithms. The brainwave discriminator, often referred to as the classifier component, can be trained in the characteristic nature of the test subject's EEG response when presented with stimulus records or targets known to be familiar to the test subject. The response to such target records provides the classifier component with exemplar characteristics to discriminate records that are not known to be known by the test subject but probe what the test subject recognizes. Alternatively, the classifier component can learn the difference between recognition and non-recognition brainwave response by observing the brainwave response to a deck containing stimuli that are not necessarily known to be known by the test subject but are likely to be recognized. Examples might include images of famous persons or an image of the test subject.

Depending upon the individual test subject and the type of stimuli presented, brainwave indications of recognition in the p-300 may vary in amplitude, character, and latency. A brainwave classifier component algorithm may correlate indications of recognition in brainwaves other than the typical p-300 to strengthen the confidence in recognition or non-recognition.

A test subject may intentionally or unintentionally create circumstances that adversely affect EEG data such that EEG recognition signals are suppressed, masked, or otherwise corrupted. A test-subject that becomes inattentive or intentionally suppresses the senses targeted by the stimuli (e.g., for visual stimuli, averting eyes from display) will not produce responses indicating recognition. Brainwave indications of inattentiveness and external indications of suppressed senses can be used to flag the recognition scoring algorithm to disregard those tests. When the test subject is again attentive to the stimuli, the recognition scores will again be useful indicators of recognition.

Likewise, intentional or unintentional masking of brainwave signals can be accomplished by muscle movements in the face and scalp. EEG signals associated with muscle movement is typically much larger than EEG signals resulting from brain functions. Signals resulting from eye blinks, jaw clinching or scalp motion can be automatically discriminated from brainwave signals and therefore used to adjust recognition scores for target and non-target stimuli.

Presentation of a particular deck may be repeated more than once to strengthen statistical confidence in the EEG indications of recognition or familiarity with particular stimuli. Shuffling the deck (i.e., reordering the target and non-target stimuli) each time it is presented ensures that the brainwave signals observed for target stimuli are due to the content of the stimulus rather than the presentation order.

The general features of this disclosure provide for an automated system that characterizes brainwave signals from the EEG data to indicate the level of recognition of stimuli presented in multiple sequences of stimuli that are presented to the test subject. The system may have access to category repositories of target stimuli and non-target stimuli. Target stimuli may represent information, which would be valuable to know that the subject possesses. Non-target stimuli represent information, which generally would not be thought to be valuable to know that the subject possesses. Automated indication of recognition of target stimuli in one deck may guide automated selection of target stimuli in subsequent decks to obtain additional detail of the subject's knowledge, interest, and experience. Within the broad target and non-target categories are further categories of stimuli, which may be classified according to the topics or subject matter to which they are related. Decks may be first presented to the test subject with stimuli that cover broad subject areas covering major divisions of a topic. Depending upon which stimuli records result in brainwave indications of recognition, subsequent decks with stimuli covering similar or related topics in greater detail and specificity may be selected and presented to the test subject to discover additional knowledge, interest, and experience FIG. 1 shows a flow diagram of an embodiment of this disclosure for a method 100 to detect knowledge of a subject by exposing the subject to stimuli and correlating certain detected brainwave responses to categories correlated with the stimuli presented. The subject is exposed to the first sequence of stimuli 105. Each stimulus of the first sequence of stimuli is correlated with a category. A brainwave response of the subject to each stimulus of the first sequence of stimuli is detected 110, and, based on the occurrence of a p-300 signal, the detected brainwave response is correlated 115 to at least one target category. In an embodiment the method may further comprise selecting a second sequence of stimuli 120, based upon the brainwave response of the subject to each stimulus of the first sequence of stimuli.

Figure 2:
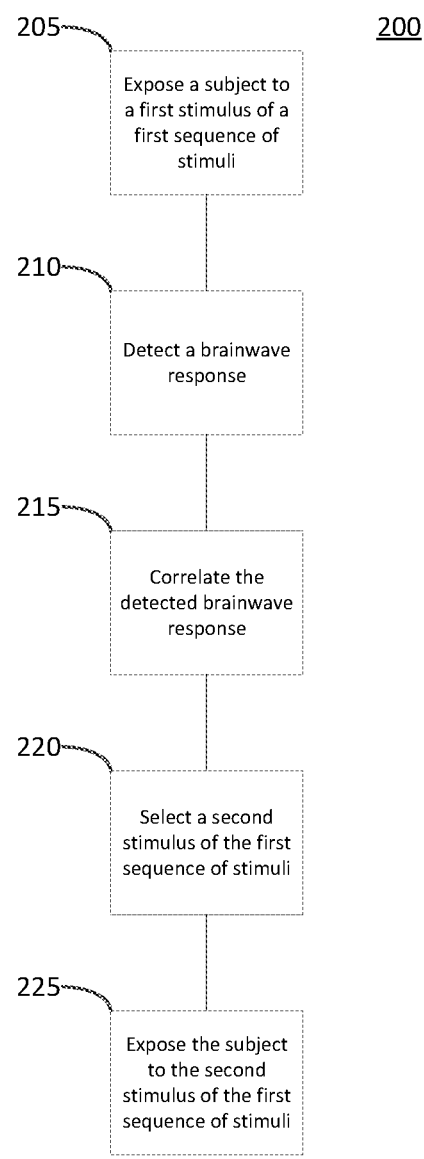
FIG. 2 shows a flow diagram for a second method for knowledge detection.

FIG. 2 shows a flow diagram of another embodiment of this disclosure for a method 200 to detect knowledge of a subject by exposing the subject to stimuli and correlating certain detected brainwave responses to categories correlated with the stimuli presented. At least one stimulus of the first sequence of stimuli is correlated with a category. In some embodiments there may be a large number of categories, such as those related to the lower levels of abstraction in the vocational knowledge discovery embodiment discussed below. The subject is exposed to a first stimulus of the first sequence of stimuli 205. A brainwave response is detected 210, and, based on the occurrence of a p-300 signal, the detected brainwave response is correlated 215 to at least one target category. A second stimulus of the first sequence of stimuli may be selected 220 and exposed 225 to the subject based upon a brainwave response to at least one prior stimulus of the first sequence of stimuli.

Figure 3:
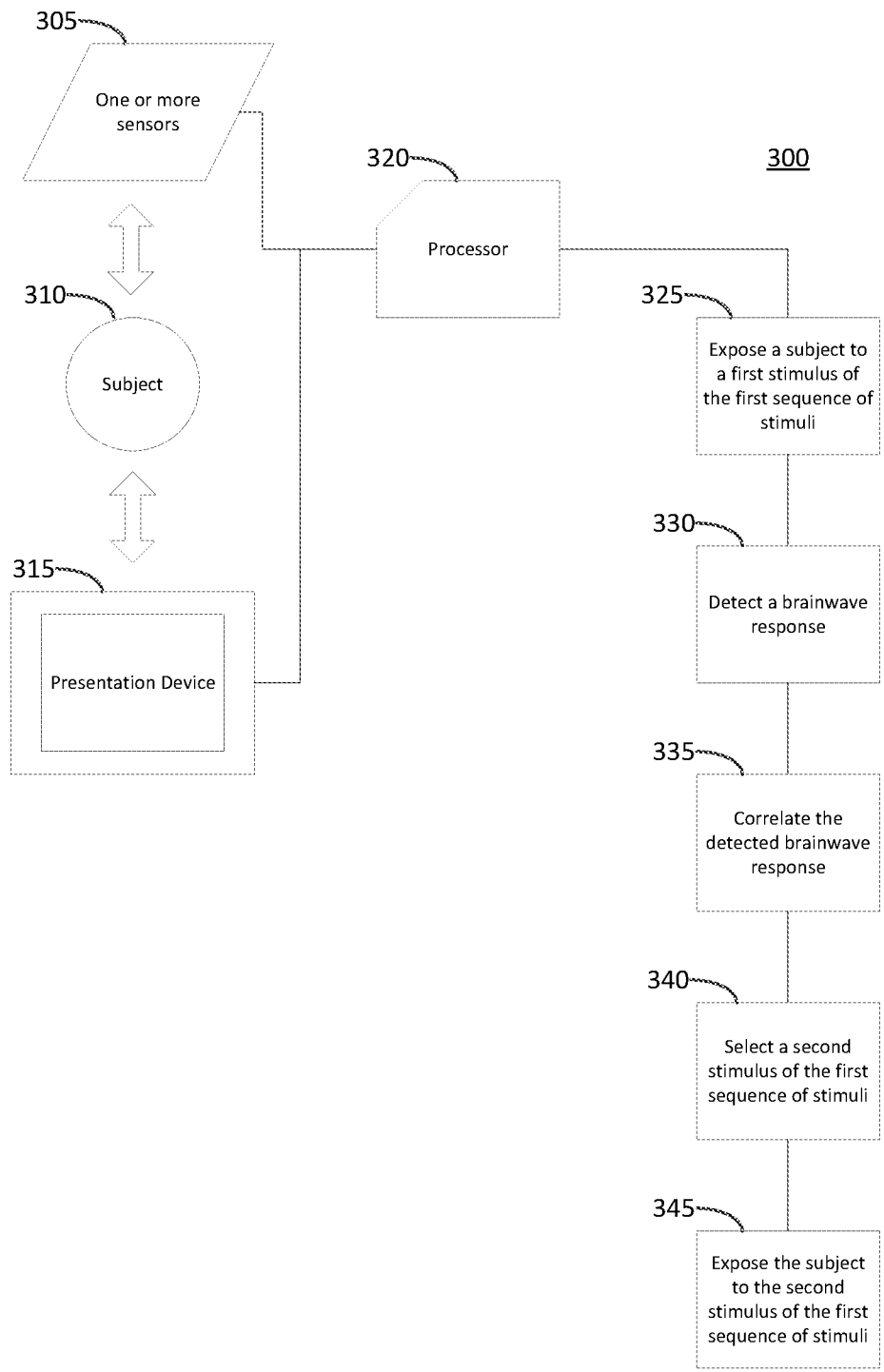
FIG. 3 shows a system diagram for a system for knowledge detection.

FIG. 3 shows a system diagram of another embodiment of this disclosure for a system 300 to detect knowledge of a subject by exposing the subject to stimuli and correlating certain detected brainwave responses to categories correlated with the stimuli presented. This embodiment includes one or more sensors 305. These sensors may be electrodes or any other component suitable for detecting EEG signals. The electrodes may be individually wired or part of a connected array. The sensors may be any that are suitable to take a reading from a human subject 310. Typically, but not necessarily, the sensors may be placed on the scalp with a conductive gel or paste. Caps or netted devices may also be used. A presentation device 315 is included, such as an audio video system, computer, or similar device capable of generating stimuli that may be experienced by a subject. The presentation device may also be any device suitable for generating smell stimuli, touch stimuli, or taste stimuli. A processor 320 is also included for executing instructions to expose the subject to a first stimulus of a first sequence of stimuli 325 through the presentation device. At least one stimulus of the first sequence of stimuli are correlated with a category. It should be understood that non-target stimuli may be similar to target stimuli for a particular subject matter category but not necessarily representative of that category. The processor detects 330 a brainwave response of the subject to each stimulus of the first sequence of stimuli and, based on the occurrence of a p-300 signal, the detected brainwave response is correlated 335 to at least one target category. A second stimulus of the first sequence of stimuli, may be selected 340 based upon a brainwave response to at least one prior stimulus of the first sequence of stimuli. And the subject may be exposed 345 to the second stimulus of the first sequence of stimuli.

More generally, a subject such as a person may be exposed to a first sequence of stimuli. The person may be exposed to the stimuli at a rate of at least 3 stimuli per second, although significantly slower rates are also contemplated herein. The first sequence can have one or more stimuli. A stimulus can be a sight stimulus, a sound stimulus, a touch stimulus, a smell stimulus, and a taste stimulus or any combination thereof. One or more than one of the stimuli in the first sequence may be associated with a category. For example, a single stimulus such as a photograph of a football game, may be associated with a category such as a "football." The category may be an occupational category, such as "football player" or "referee." Likewise, a group of stimuli may be associated with a category. For example, a photograph showing a football game, a photograph showing a bicycle race and a photograph showing a tennis match may be associated as a group with a category, such as "sports." The category may be an occupational category, such as "athlete."

A brainwave response of the subject to stimuli can be detected using sensors. The response may be a p-300 signal. The response can be correlated to at least one target category. A second sequence of stimuli may be selected based upon the brainwave response to one or more stimuli in the first sequence. The second stimuli may be selected automatically or by a user. The first sequence of stimuli can be a baseline sequence.

Proper assembly of the sequence of a deck is a key contributor of the certain embodiments of this disclosure. A test deck may be composed of (i) a small number of target stimuli used to probe the test subject's familiarity on a topic or range of topics and (ii) a larger number of non-target items unlikely to be recognized by the test subject but similar in gross characteristics of the target items. For example, the ratio of target to non-target items may range between 1:25 to 1:2. When the targets are used to isolate topics of familiarity in a deck that covers a broad range of topics the ratio of targets to non-targets can be larger because many more of the intended probing target stimuli will also be unfamiliar to the test subject. The size of decks at a particular level of abstraction can be small or large. The deck may be broken into subsets or hands to accommodate the attention span of the test subject or allow more frequent periods of rest between hands.

As stated above, comparison of the brainwave response for target and non-target stimuli provides insight into the test subject's knowledge. In an embodiment where the stimuli are images, target and non-target images in the deck may be selected from images of people, places, things, numbers, letters, words, and symbols. Target and non-target images in the deck are selected to be similar in physical attributes such as size, color, resolution, and composition. In an embodiment where the stimuli are sound stimuli, examples may include audio clips, voice, music, and the sounds that relevant things make. Similar to visual presentation decks, sound decks are more diagnostic if target and non-target clips are similar in attributes such as volume level and background noise levels. This minimizes the occurrence psychophysiological responses that can be more strongly associated with surprise or startle than with the desired response of recognition.

Figure 6:
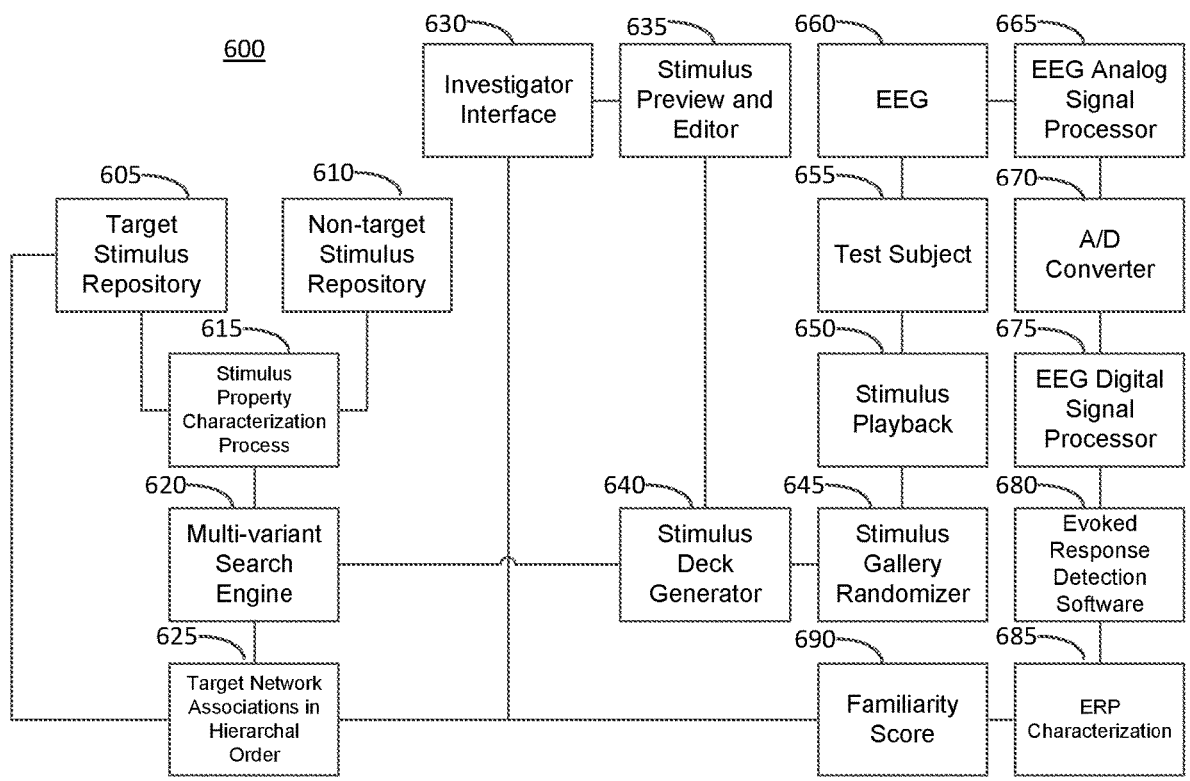
FIG. 6 shows a system diagram of an embodiment of this disclosure related to automated generation of stimulus sequences.

Decks designed to explore the depth and breadth of familiarity of a particular category can be compiled beforehand or created on the fly by an automated system that employs machine learning techniques to populate new decks of stimuli based on indications of familiarity observed in previous decks of stimuli. FIG. 6 depicts one embodiment wherein new decks may be generated to validate what was indicated as familiar in earlier decks and introduce new stimuli that probe a deeper level of knowledge on topics of familiarity. FIG. 6 shows a system diagram 600, where target stimuli 605 and non-target stimuli 610 may be characterized by characterization process 615 and made accessible to search engine 620. Stimulus deck generator 640 draws a sequence of stimuli from the search engine and sends the sequence to the randomizer 645. Optionally, a user may access the sequence of stimuli through the investigator interface 630 and edit the sequence through the editor 635. The stimuli are then presented 650 to the subject 655, and the subject's EEG signals are collected 660, analog processed 665, converted 670, and digitally processed 675. The p-300 signal may be detected 680, characterized 685, scored 690, and entered into a hierarchy of scores 625 for target stimuli. The stimulus deck generator can then draw on the previous target hierarchy to generate more relevant decks for further presentation to the subject. For Example, the stimulus deck generator may select target stimuli of the same categories as those that are near the top of the target stimuli hierarchy. This process may also be performed after each stimulus is presented, such that the deck generator may continuously improve the relevancy of the target stimulus to be presented within a given deck.

Figure 4:
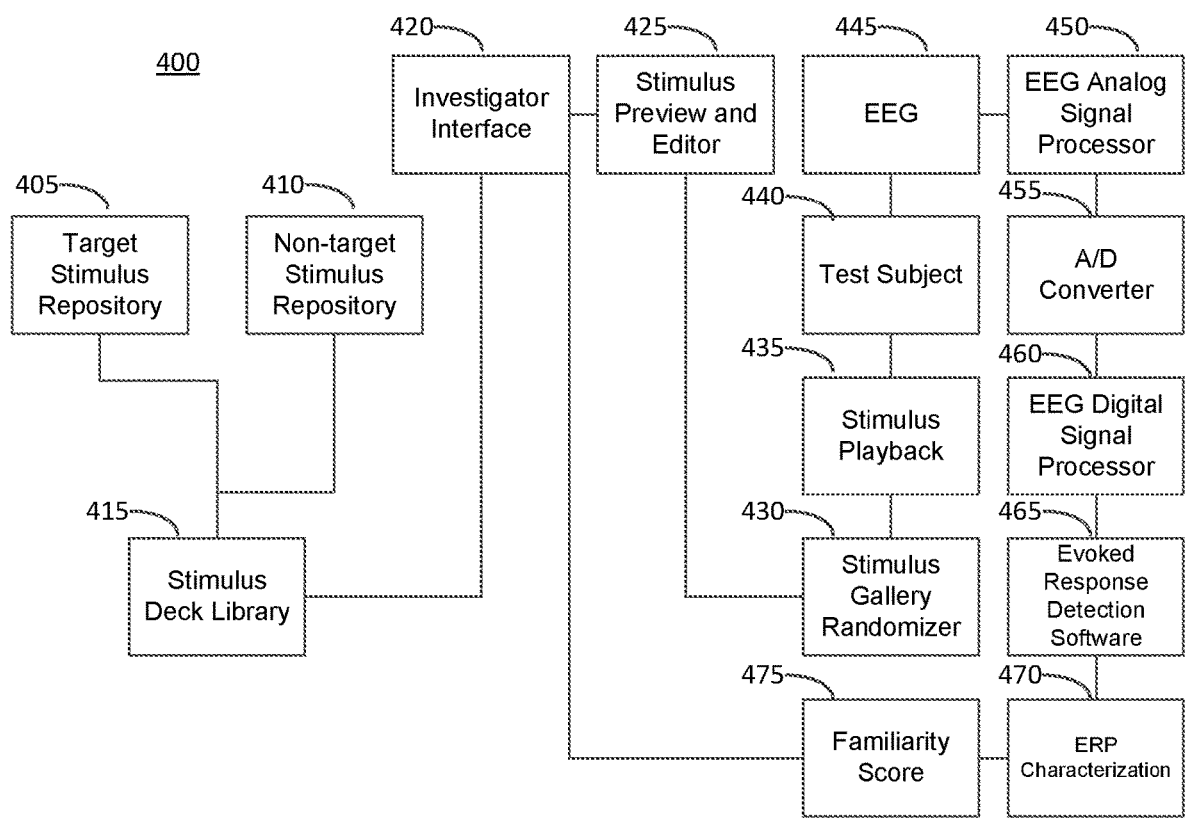
FIG. 4 shows a system diagram of an embodiment of this disclosure related to vocational knowledge discovery.

Alternatively, it may be advantageous for the deck to be manually compiled by a user (e.g., an investigator). FIG. 4 depicts one such embodiment. In this system diagram embodiment 400, a user may compile a stimulus deck by accessing, through investigator interface 420, the stimulus deck library 415 that draws on target stimuli 405 and non-target stimuli 410. The investigator may compile and edit the deck via editor 425 and then enter the deck into randomizer 430. The stimuli are then presented 435 to the subject 440, and the subject's EEG signals are collected 445, analog processed 450, converted 455, and digitally processed 460. The p-300 signal may be detected 465, characterized 470, and scored 475. The user then has access to the scoring through the investigator interface.

Figure 7:
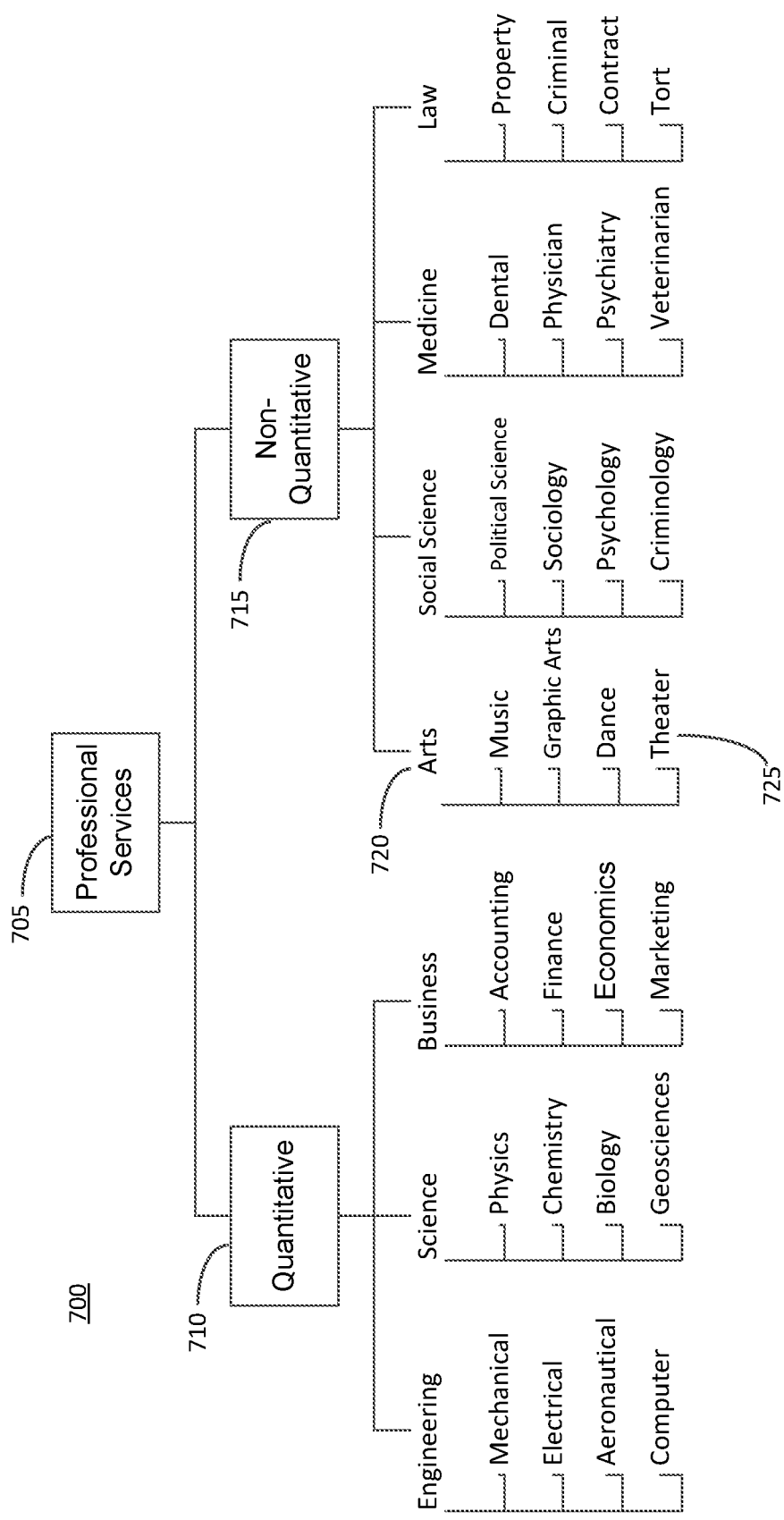
FIG. 7 shows a system diagram of an embodiment of this disclosure for vocational knowledge detection.

As shown in FIG. 7 and discussed below, another embodiment of this disclosure is described in relation to vocational knowledge detection 700. The purpose of this example is to identify the profession of a test subject.

Multiple decks of stimuli are presented to the test subject at various levels of abstraction or detail in order to guide selection of topics of later decks with increased level of detail, and which further narrow the scope of the search. The lower level decks 720 have increased resolution and specificity of characteristics or knowledge unique to specific professions. In this example, the first level of abstraction is to determine if the test subject operates in a quantitative 710 or non-quantitative 715 division of professions—a very high level of abstraction. From there, decks are presented to the test subject to determine which category of profession (e.g. 720) within the quantitative or non-quantitative division the test subject operates. Examples of professional disciplines are engineering, medicine or the arts. Once the category is determined, decks of stimuli for specific professions (e.g. 725) such as mechanical engineer, graphical artist or criminal lawyer are present to establish the specific profession of the test subject. This simple three-tiered example (i.e., division, discipline, and specific profession) is not intended to describe the full breadth and depth of potential vocational applications.

At the highest level of abstraction, the division level, test decks are compiled to establish quantitative or non-quantitative division of professions. Example content of decks of target stimuli might include: names of principal concepts or persons key to specific professional disciplines, technical terms unique with quantitative and non-quantitative disciplines, fundamental equations used in quantitative professional disciplines, mathematical constants used in the quantitative professions, symbols commonly used in quantitative and non-quantitative disciplines, or acronyms commonly used in quantitative and non-quantitative disciplines. If the dealer is a user, she can be in close proximity with the test subject as the decks are presented. Alternatively, the dealer may be located remotely and monitor events by electronic communications.

This approach to vocational evaluation does not rely on binary decision of familiar or not familiar with a particular person, place, or thing as in the GKT. Instead, this technique uses multiple steps with increasing level of detail to discover the profession of a test subject without knowing anything about the test subject beforehand. The progression to each lower level of detail is guided by the positive response of familiarity with one or more targets in the test deck at a higher level of abstraction to discover areas of interest and knowledge. Based upon response to stimuli, the administrator (the dealer) selects another deck to ascertain familiarity with increased detail to further refine the depth and breadth of familiarity with related topics. As discussed above, the dealer can be a user or automated.

In another embodiment, an EEG system is disclosed, comprising: sensors, amplifiers, analog filters, A/D converters, digital filters, noise rejection components, and signal extraction processing components; a stimulus presentation system capable of reproducing images, video, and sounds, synchronized in time with the sensors, implemented with one or more decks of analog or digital stimulus files which are reproduced serially for reception by human senses and illicit psychophysiologic response recorded by the EEG system, wherein the stimulus decks are presented systematically in order of broad divisions of information to progressively greater detail and specificity to discover vocational knowledge, interest and experience, configured such that indication of recognition of stimuli in one deck guides selection of subsequent decks to obtain additional detail on vocational knowledge, interest and experience; and an automated analysis system that extracts and characterizes brainwave signals indicative of recognition of reproduced by the stimuli presentation system.

In this embodiment, additional senses may be reproduced and presented to the test subject, including taste, smell and touch; the stimulus deck may be created by hand or by machine; the stimulus deck may be created before presentation or in real-time based on indications of recognition in previous stimulus decks; the dealing the deck may be controlled by a dealer or be automated; dealer control (in person or automation) may be proximal with the test subject or from a remote location; and/or the system may assess the level of test-subject cooperation and adjust recognition scores accordingly.

Lastly, in a final embodiment, this invention teaches a system capable of deducing the vocation of an individual without prior knowledge and without engaging a person in verbal questions. The system is composed of an EEG subsystem, a stimulus presentation subsystem, a system of stored records of stimuli and an automated data processing subsystem. The EEG subsystem is composed of multiple channels of sensors, amplifiers, analog filters and analog-to-digital converters. The stimulus presentation subsystem is capable of reproducing multiple records of images, video, or sounds stored in analog or digital files that form decks of stimulus data. The stimulus presentation system is synchronized with the EEG system so that the time of presentation and identity of the stimulus record are associated with the EEG data. Stimulus files in a deck are reproduced serially at a rapid pace for exposure to human senses which result in a psychophysiologic response sensed and recorded by the EEG subsystem. The automated data processing system extracts and characterizes brainwave signals from EEG data to indicate the level of recognition of each stimulus. Multiple stimulus decks are presented in a systematic approach starting with broad divisions of information to progressively greater detail and specificity to discover vocational knowledge, interest, and experience of the person being monitored. Indication of recognition of stimuli in one deck guides automated selection of subsequent decks to obtain additional detail on vocational knowledge, interest, and experience.

All or part of the systems and methods described herein may be implemented as a computer program product that is a non-transitory computer-readable storage medium encoded with computer code that is executable by a processor. All or part of the systems and methods described in this application may be implemented as an apparatus, method, or electronic system that may include one or more processors and storage devices that store executable computer program code to implement the stated functions.

The details of one or more embodiments of the subject matter of this application are set forth in the drawings and descriptions contained in this application. Other features, aspects, and advantages of the subject matter will become apparent from the description above, drawings, and claims.

The subject matter of this specification functions in a variety of component combinations and contemplates all those types of components a person of ordinary skill in the art would find suitable for functions performed. The figures describe specific components in specific embodiments. However the range of the types of components mentioned in the description of the figures may be applied to other embodiments as well.

The terminology used herein is for the purpose of describing particular embodiments only and is not intended to be limiting. As used herein, the singular forms "a," "an," and "the" are intended to include the plural forms as well, unless the context clearly indicates otherwise. The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The subject matter of this specification is described above with reference to system diagrams, flow diagrams, and screen mockups of systems, methods, and computer program products. Each block or combinations of blocks in the diagrams can be implemented by computer program code and may represent a module, segment, or portion of code. Program code may be written in any combination of one or more programming languages, including object oriented programming languages such as the JAVA®, SMALLTALK®, C++, C #, OBJECTIVE-C® programming languages and conventional procedural programming languages, such as the "C" programming language.

It should be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block or combination of blocks in the diagrams can be implemented by special purpose hardware-based systems that perform the specified functions or acts.

Computer program code may be provided to a processor or multiple processors of a computer to produce a particular machine, such that the program code, which executes via the processor, create means for implementing the functions specified in the system diagrams, flow diagrams, and screen mockups.

The subject matter of this specification may be implemented on one or more physical machines. Each physical machine may be a computer comprising one or more processors and one or more storage devices; however a single processor and a single storage device are sufficient. A person of ordinary skill in the art will recognize the variety of types of computers suitable for the functions described, including desktops, laptops, handset devices, smartphones, tablets, servers, or accessories incorporating computers such as watches, glasses, or wearable computerized shoes or textiles. A non-exhaustive list of specific examples of computers includes the following: Dell ALIENWARE™ desktops, Lenovo THINKPAD® laptops, SAMSUNG™ handsets, Google ANDROID™ smartphones, Apple IPAD® tablets, IBM BLADECENTER® blade servers, PEBBLE™ wearable computer watches, Google GLASS™ wearable computer glasses, or any other device having one or more processors and one or more storage devices, and capable of functioning as described in this application.

A processor may be any device that accepts data as input, processes it according to instructions stored in a storage component, and provides results as output. A person of ordinary skill in the art will recognized the variety of types of processors suitable for the functions disclosed, including general purpose processing units and special purpose processing units. A non-exhaustive list of specific examples of processors includes the following: Qualcomm SNAPDRAGON™ processors; Nvidia TEGRA® 4 processors; Intel CORE™ i3, i5, and i7 processors; TEXAS INSTRUMENTS™ OMAP4430; ARM® Cortex-M3; and AMD OPTERON™ 6300, 4300, and 3300 Series processors. Each computer may have a single processor or multiple processors operatively connected together (e.g. in the "cloud").

A storage device is any type of non-transitory computer readable storage medium. A person of ordinary skill in the art will recognized the variety of types of storage devices suitable for the functions disclosed, including any electronic, magnetic, optical, electromagnetic, infrared, or semiconductor system or device, so long as it does not reduce to a transitory or propagating signal. A non-exhaustive list of specific examples of storage devices includes the following: portable computer diskettes, hard disks, random access memory, read-only memory, erasable programmable read-only memory, flash memory, optical fibers, portable compact disc read-only memory, optical storage devices, and magnetic storage devices. Each computer may have a single storage device or multiple storage devices operatively connected together (e.g. in the "cloud").

This disclosure may be implemented on one or more computers running one or more instances of a virtual machine. A virtual machine is a software implementation of a computer that executes programs like a physical machine. Thus a single physical machine may function conventionally as a physical computer, while also implementing a virtual machine that can perform the same processes as the physical computer. Multiple instances of a virtual machine may run on one computer or across multiple computers. A person of ordinary skill in the art will recognize the variety of types of virtual machines suitable for the functions disclosed, including system level virtual machines, process level virtual machines, fictive computers, and distributed computers. A non-exhaustive list of specific examples of virtual machines includes the following: VMWARE® virtual machines and Oracle VM VIRTUALBOX™ virtual machines.

Embodiments of this disclosure that employ virtual machines may contain a hypervisor, which is also known as a virtual machine monitor. A hypervisor is a piece of computer software that creates, runs, and manages virtual machines. More than one virtual machine may be run by a single hypervisor. The hypervisor controls the utilization of one or more processors by one or more virtual machines and the utilization of one or more storage devices by one or more virtual machines. A person of ordinary skill in the art will recognized the variety of types of hypervisors suitable for the functions disclosed, including type one or "native" hypervisors, and type two or "hosted" hypervisors. A non-exhaustive list of specific examples of hypervisors includes: Oracle VMWARE® Server for SPARC, Oracle VM SERVER™ for x86, Citrix XENSERVER™, and VMWARE® ESX/ESXi.

For the purposes of this application, the term "computing component" means a computer, a virtual machine, or multiple computers or virtual machines functioning as a single component. The term "computer" is limited to physical machines. Generally a computer functions as a computing component by implementing an operating system through which program code, which implements the methods of this system, is executed. Generally, when a virtual machine functions as a computing component, a computer implements a hypervisor which implements a separate operating system, through which the program code is executed.

As referenced above, a single computer may implement multiple computing components, wherein the computer itself functions as a computing component and concurrently implements one or more instances of a virtual machine. Each virtual machine functions as a separate computing component. Similarly, a plurality of computing components may be made up of separate computers, none of which implement a virtual machine, or a plurality of computing components may be implemented on a single computer wherein only the virtual machines function as computing components. Additional combinations are contemplated as well, such as where a computing component is implemented across multiple computers. For example, a hypervisor of a virtual machine may manage the processors and storage devices of three computers to implement a virtual machine that functions as a single computing component. A person of ordinary skill in the art will recognize the range of combinations of computers and virtual machines that are suitable for the functions disclosed.

Computing components may be operatively connected to one another or other devices, such as by a communications network. One skilled in the art will recognize the appropriate media over which multiple computing components may be operatively connected to each other in a manner suitable for the functions disclosed, including as a communications network that allows the computing components to exchange data such that a process in one computing component is able to exchange information with a process in another computing component. A non-exhaustive list of specific examples of transmission media includes: serial or parallel bus systems, wireless, wireline, twisted pair, coaxial cable, optical fiber cable, radio frequency, microwave transmission, or any other electromagnetic transmission media.

The above components are described in greater detail with reference to the figures. The descriptions set forth the various processes, relationships, and physical components of various embodiments of the subject matter of this disclosure.

The invention claimed is:

1. A method for obtaining information of at least one of knowledge, interest and experience of a subject for a specific category of knowledge, the method comprising:
   receiving, by a processor, a first signal, wherein the first signal represents a first brainwave response of the subject to a first stimulus associated with first information;
   determining, by the processor, a first correlation between the first brainwave response and a knowledge category, wherein the knowledge category is a first node of a hierarchical tree structure for categories of knowledge;
   receiving, by the processor and after a determination of the first correlation, a second signal, wherein the second signal represents a second brainwave response of the subject to a second stimulus associated with second information in greater detail and specificity than the first information;
   determining, by the processor, a second correlation between the second brainwave response and a sub-category of the knowledge category, wherein the sub-category is a second node representing the specific category of knowledge of the hierarchical tree structure for the categories of knowledge; and
   obtaining information of at least one of knowledge, interest and experience of the subject based on the determined second correlation between the second brainwave response and the sub-category of the knowledge category.

2. The method of claim 1, wherein at least one of the first signal or the second signal comprises an electroencephalogram.

3. The method of claim 1, wherein at least one of:
   the receiving the first signal comprises receiving the first signal from a sensor; or
   the receiving the second signal comprises receiving the second signal from the sensor.

4. The method of claim 3, where in the sensor comprises an electrode.

5. The method of claim 1, wherein at least one of:
   the determining the first correlation comprises determining a presence of a p-300 signal at a point in the first signal that has a correspondence with a time at which the subject was exposed to the first stimulus; or
   the determining the second correlation comprises determining a presence of the p-300 signal at a point in the second signal that has a correspondence with to a time at which the subject was exposed to the second stimulus.

6. The method of claim 5, wherein at least one of:
   the correspondence with the time at which the subject was exposed to the first stimulus comprises the point in the first signal being about 300 milliseconds after the time at which the subject was exposed to the first stimulus; or
   the correspondence with the time at which the subject was exposed to the second stimulus comprises the point in the second signal being about 300 milliseconds after the time at which the subject was exposed to the second stimulus.

7. The method of claim 1, wherein at least one of:
   the determining the first correlation comprises processing the first signal through a classifier; or
   the determining the second correlation comprises processing the second signal through the classifier.

8. The method of claim 7, further comprising training, by the processor, the classifier with a signal produced in response to exposing the subject to at least one of a stimulus known to be familiar to the subject or a stimulus known to be recognized by the subject.

9. The method of claim 1, further comprising determining, by the processor, a correlation between at least one of the first brainwave response or the second brainwave response and an indication of at least one of:
   an inattentiveness of the subject to at least one of the first stimulus or the second stimulus; or
   a muscle movement by the subject at a time of at least one of the first stimulus or the second stimulus.

10. The method of claim 1, wherein at least one of the first stimulus or the second stimulus excludes a question presented to the subject.

11. The method of claim 1, wherein at least one of the first stimulus or the second stimulus is included in a sequence of stimuli.

12. The method of claim 11, wherein the sequence of stimuli is presented to the subject at a rate of between four and twelve stimuli per second.

13. The method of claim 11, further comprising repeating, by the processor and in iterations, at least one of the receiving the first signal or the receiving the second signal, wherein at least one of:
- a position of the first stimulus in a first iteration is different from a position of the first stimulus in a second iteration; or
- a position of the second stimulus in the first iteration is different from a position of the second stimulus in the second iteration.

14. The method of claim 1, further comprising selecting, by the processor and after the determination of the first correlation, the second stimulus.

15. A non-transitory computer-readable medium storing computer code for obtaining information of at least one of knowledge, interest and experience of a subject for a specific category of knowledge, the computer code including instructions to cause the processor to:
- receive a first signal, wherein the first signal represents a first brainwave response of the subject to a first stimulus associated with first information;
- determine a first correlation between the first brainwave response and a knowledge category, wherein the knowledge category is a first node of a hierarchical tree structure for categories of knowledge;
- receive, after a determination of the first correlation, a second signal, wherein the second signal represents a second brainwave response of the subject to a second stimulus associated with second information in greater detail and specificity than the first information;
- determine a second correlation between the second brainwave response and a sub-category of the knowledge category, wherein the sub-category is a second node representing the specific category of knowledge of the hierarchical tree structure for the categories of knowledge; and
- obtain information of at least one of knowledge, interest and experience of the subject based on the determined second correlation between the second brainwave response and the sub-category of the knowledge category.

16. A system for obtaining information of at least one of knowledge, interest and experience of a subject for a specific category of knowledge, the system comprising:
- a memory configured to store a first signal and a second signal; and
- a processor configured to:
  - receive the first signal, wherein the first signal represents a first brainwave response of the subject to a first stimulus associated with first information;
  - determine a first correlation between the first brainwave response and a knowledge category, wherein the knowledge category is a first node of a hierarchical tree structure for categories of knowledge;
  - receive, after a determination of the first correlation, the second signal, wherein the second signal represents a second brainwave response of the subject to a second stimulus associated with second information in greater detail and specificity than the first information;
  - determine a second correlation between the second brainwave response and a subcategory of the knowledge category, wherein the sub-category is a second node representing the specific category of knowledge of the hierarchical tree structure for the categories of knowledge; and
  - obtain information of at least one of knowledge, interest and experience of the subject based on the determined second correlation between the second brainwave response and the sub-category of the knowledge category.

17. The system of claim 16, wherein at least one of:
the processor is configured to determine the first correlation by determining a presence of a p-300 signal at a point in the first signal that has a correspondence with a time at which the subject was exposed to the first stimulus; or
the processor is configured to determine the second correlation by determining a presence of the p-300 signal at a point in the second signal that has a correspondence with to a time at which the subject was exposed to the second stimulus.

18. The system of claim 17, wherein at least one of:
the correspondence with the time at which the subject was exposed to the first stimulus comprises the point in the first signal being about 300 milliseconds after the time at which the subject was exposed to the first stimulus; or
the correspondence with the time at which the subject was exposed to the second stimulus comprises the point in the second signal being about 300 milliseconds after the time at which the subject was exposed to the second stimulus.

19. The system of claim 16, wherein at least one of:
the processor is configured to determine the first correlation by processing the first signal through a classifier; or
the processor is configured to determine the second correlation by processing the second signal through the classifier.

20. The system of claim 19, wherein the processor is further configured to train the classifier with a signal produced in response to exposing the subject to at least one of a stimulus known to be familiar to the subject or a stimulus known to be recognized by the subject.

21. The system of claim 16, wherein the processor is further configured to determine a correlation between at least one of the first brainwave response or the second brainwave response and an indication of at least one of:
- an inattentiveness of the subject to at least one of the first stimulus or the second stimulus; or
- a muscle movement by the subject at a time of at least one of the first stimulus or the second stimulus.

22. The system of claim 16, wherein the processor is further configured to select, after the determination of the first correlation, the second stimulus.

* * * * *